United States Patent [19]

Okamura et al.

[11] Patent Number: 5,061,594

[45] Date of Patent: Oct. 29, 1991

[54] HIGH CONTRAST SILVER HALIDE MATERIAL CONTAINING NOVEL HYDRAZINE NUCLEATING AGENT

[75] Inventors: Hisashi Okamura; Kazunobu Katoh, both of Kanagawa, Japan

[73] Assignee: Fuji Photo Film Co., Ltd., Kanagawa, Japan

[21] Appl. No.: 470,496

[22] Filed: Jan. 26, 1990

[30] Foreign Application Priority Data

Jan. 27, 1989 [JP] Japan .................................. 1-018378

[51] Int. Cl.$^5$ .............................................. G03C 1/06
[52] U.S. Cl. .................................. 430/264; 430/598; 430/600
[58] Field of Search ............... 430/264, 598, 599, 600, 430/223

[56] References Cited

U.S. PATENT DOCUMENTS

| | | | |
|---|---|---|---|
| 4,816,373 | 3/1989 | Ohashi et al. | 430/264 |
| 4,977,063 | 12/1990 | Usagawa et al. | 430/264 |
| 5,006,445 | 4/1991 | Yagihara et al. | 430/598 |

FOREIGN PATENT DOCUMENTS

| | | | |
|---|---|---|---|
| 0283040 | 9/1988 | European Pat. Off. | 430/598 |
| 0286840 | 10/1988 | European Pat. Off. | 430/598 |
| 0330109 | 8/1989 | European Pat. Off. | 430/598 |
| 1213847 | 3/1985 | Japan | 430/598 |

Primary Examiner—Charles L. Bowers, Jr.
Assistant Examiner—Thomas R. Neville
Attorney, Agent, or Firm—Sughrue, Mion, Zinn, Macpeak & Seas

[57] ABSTRACT

A silver halide photographic material which comprises a support having thereon at least one hydrophilic colloid layer being a silver halide photographic emulsion layer, and at least one hydrophilic colloid layer containing a compound represented by the following general formula (I):

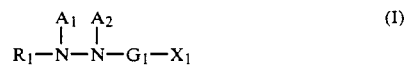

wherein $A_1$ and $A_2$ both represent a hydrogen atom, or one of $A_1$ and $A_2$ is a hydrogen atom and the other is a sulfonyl group or an acyl group; $R_1$ represents an aliphatic group or an aromatic group; $G_1$ represents a carbonyl group, a sulfonyl group, a sulfinyl group, a sulfoxy group, a group of

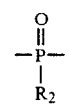

wherein $R_2$ is an alkoxy group or an aryloxy group, a group of

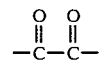

or an iminomethylene group; $X_1$ represents a residue of a nitrogen-containing heterocyclic ring; and at least one of $R_1$ and $X_1$ having an adsorption-accelerating group on silver halide.

9 Claims, No Drawings

HIGH CONTRAST SILVER HALIDE MATERIAL CONTAINING NOVEL HYDRAZINE NUCLEATING AGENT

FIELD OF THE INVENTION

This invention relates to a silver halide photographic material which gives an extremely high contrast negative image, a high-sensitivity negative image and a dot image of good quality, and to a silver halide photographic material capable of forming direct positive image. More particularly, it relates to a photographic material which contains a novel compound as a nucleating agent for the silver halide.

BACKGROUND OF THE INVENTION

It is known to add hydrazine compounds to silver halide photographic emulsions or developing solutions. For example, the addition of hydrazine compounds to silver halide photographic emulsions or developing solutions is disclosed in U.S. Pat. No. 3,730,727 (developing solution containing a combination of ascorbic acid and hydrazine), U.S. Pat. No. 3,227,552 (the use of hydrazine as an auxiliary developing agent to obtain direct positive color image), U.S. Pat. No. 3,386,831 (silver halide light-sensitive material containing β-monophenylhydrazide of an aliphatic carboxylic acid as a stabilizer), U.S. Pat. No. 2,419,975 and Mees, *The Theory of Photographic Process*, the third edition, (1966), page 281.

In particular, U.S. Pat. No. 2,419,975 discloses a method for obtaining high contrast negative image by adding hydrazine compounds.

In the specification of that patent, it is disclosed that extremely high-contrast photographic characteristics having a gamma (γ) value exceeding 10 can be obtained when hydrazine compounds are added to silver chlorobromide emulsions, and when photographic materials are processed with developing solutions having a pH of as high as 12.8. However, strongly alkaline developing solutions having a pH near 13 are liable to be oxidized by air. They are therefore unstable and can not be stored or used over a long period of time.

Superhigh-contrast photographic characteristics having a gamma value exceeding 10 are useful for the reproduction of line drawing and for the photographic reproduction of continuous image by dot image useful for printing plate making in the case of both negative and positive images.

To achieve this object, there have been conventionally used methods wherein photographic emulsions comprising silver chlorobromide having a silver chloride content of higher than 50 mol %, preferably 75 mol % are used and development is carried out with hydroquinone developing solutions containing sulfite ion at an extremely low effective concentration (generally not higher than 0.1 mol/l). However, the low concentration of sulfite ion in the developing solutions results in the developing solutions being very unstable and being preserved for only 3 days at the most. Further, silver chlorobromide emulsions having a relatively high silver chloride content must be used and hence high sensitivity cannot be obtained. Accordingly, there has been a demand to obtain superhigh-contrast photographic characteristics useful for the reproduction of dot image or line drawing by using high-sensitivity emulsions and stable developing solutions.

U.S. Pat. Nos. 4,224,401, 4,168,977, 4,243,739, 4,272,614 and 4,323,643 disclose silver halide photographic emulsions which give extremely high-contrast negative photographic characteristics with stable developing solutions. However, it has been found that the acyl hydrazine compounds used therein have certain disadvantages.

Namely, it is known that these hydrazine compounds evolve nitrogen gas during development. The gas is accumulated in the film to form bubbles which damage the photographic image. Further, the gas flows into the developing solutions so that other photographic materials are adversely affected.

It is known that increasing the molecular weights of nucleating agents, to thereby make the agents nondiffusing, is a means for preventing gas from flowing into the developing solutions. However, it has been found that conventional nucleating agents which were made nondiffusing in this manner, reduce the stability of emulsions over time. Namely, when coating solutions containing those nucleating agents are left to stand, precipitates are formed in the coating solutions, filterability deteriorates and further photographic performance causes change.

Furthermore, these conventional hydrazine compounds must be used in large quantities for the purposes of sensitization and imparting high contrast. They also generally cause sensitization and an increase in fogging with time during storage when high-sensitivity photographic materials in particular are required and when the hydrazine compounds are used in combination with other sensitizing techniques (e.g., an increase in chemical sensitization; an increase in grain size; and the addition of compounds which accelerate sensitization as described in U.S. Pat. Nos. 4,272,606 and 4,241,164).

Accordingly, there has been a demand for compounds which reduce the evolution of bubbles or the outflow of gas into the developing solutions do not have a problem with respect to stability with time, and give extremely high contrast photographic characteristics by the use of a very small amount thereof.

U.S. Pat. Nos. 4,385,108, 4,269,929 and 4,243,739 disclose that extremely high contrast negative gradation photographic characteristics can be obtained by using hydrazine compounds having substituents which can be easily adsorbed by silver halide grains.

Among these hydrazine compounds having adsorptive groups, those exemplified in the above patent specifications have the disadvantage that they cause desensitization with time during storage. Hence, it is necessary to choose compounds which do not cause the above-described problem.

On the other hand, many direct positive photographic processes are known. Among them, the most useful are (1) a process wherein silver halide grains previously fogged are exposed in the presence of a desensitizer and then development is carried out and (2) a process wherein silver halide emulsions having sensitivity speck predominantly in the interior of silver halide grains are exposed and then development is carried out in the presence of a nucleating agent. The present invention relates to the latter process. A silver halide emulsion in which sensitivity speck exists predominantly in the interiors of silver halide grains and a latent image is predominantly formed in the interiors of the grains, is called an internal latent image type silver halide emulsion which can be distinguished from silver halide grains in which a latent image is predominantly formed on the surfaces of the grains.

There are known methods for obtaining direct positive image by subjecting the internal latent image type silver halide emulsion to surface development in the presence of a nucleating agent and photographic emulsions and photographic materials used for said methods, as disclosed in *Research Disclosure*, No. 23510 (November, 1983).

In the above methods for obtaining a direct positive image, nucleating agents may be added to developing solutions, but good reversal characteristics can be obtained when the nucleating agents are adsorbed on the surfaces of silver halide grains by adding the agents to the photographic emulsion layers of the photographic material or to the other appropriate layers thereof.

Examples of nucleating agents used in the above processes for obtaining a direct positive image are hydrazine compounds described in U.S. Pat. Nos. 2,563,785 and 2,588,982; hydrazide and hydrazine compounds described in U.S.. Pat. No. 3,227,552; heterocyclic quaternary salt compounds described in U.S. Pat. Nos. 3,615,615, 3,719,494, 3,734,738, 4,094,683 and 4,115,122, British Patent 1,283,835, JP-A-52-3426 (the term "JP-A" as used herein means an "unexamined published Japanese patent application") and JP-A-52-69613; thio urea linking type acylphenyl hydrazine compounds described in U.S. Pat. Nos. 4,030,925, 4,031,127, 4,139,387, 4,245,037, 4,255,511 and 4,276,364 and British Patent 2,012,443; compounds having a heterocyclic thioamido group on the adsorption group described in U.S. Pat. No. 4,080,207; phenylacylhydrazine compounds having mercapto group-containing heterocyclic groups as the adsorption group described in British Patent 2,011,397B; sensitizing dyes having a substituent having a nucleating effect in the molecular structure described in U.S. Pat. No. 3,718,470; and hydrazine compounds described in JP-A-59-200230, JP-A-59-212828, JP-A-59-212829 and *Research Disclosure*, No. 23510 (November, 1983).

However, it has been found that all of these compounds have disadvantages. For example, some compounds are low in activity as a nucleating agent; those having high activity are poor in preservability; some compounds cause a change in activity between the time that the compound is added to the emulsion and the time that the emulsion is coated onto a support; and the quality of the layers deteriorates when large amounts of the compounds are added.

With the purpose of solving these problems, there have been proposed adsorption-type hydrazine derivatives described in JP-A-60-179734, JP-A-61-170733, JP A-62-65034, JP-A-62-948, and JP-A-61-270744, hydrazine derivatives having a heterocyclic aromatic ring in the molecular structure described in JP-A-62-275247; and hydrazine derivatives having a modifying group described in JP-A-62-270948 and JP-A-63-29751. However, all of these compounds have disadvantages. For example, the nucleating activity is insufficient for the requirement of lowering the pH of processing solutions to increase the stability of developing solutions (namely to prevent developing agents from being deteriorated), and for the requirement of shortening the processing time of development to reduce dependence on variation of the composition of the developing solutions (e.g., pH, sodium sulfite). Or they cause an adverse effect by the outflow thereof into the developing solutions.

SUMMARY OF THE INVENTION

Accordingly, a first object of the present invention is to provide a silver halide photographic material which can give extremely high-contrast negative gradation photographic characteristics having a gamma value exceeding 10 with stable developing solutions.

A second object of the present invention is to provide a negative type silver halide photographic material containing a high-activity hydrazine compound which can give an extremely high-contrast negative gradation photographic characteristic even with developing solutions having a low pH value by the use of a small amount thereof without having an adverse effect on photographic characteristics.

A third object of the present invention is to provide a direct positive type silver halide photographic material containing a high-activity hydrazine compound which gives excellent reversal characteristics even with developing solutions having a low pH value.

A fourth object of the present invention is to provide a silver halide photographic material containing a hydrazine compound which can be easily synthesized, is excellent in preservability and has good long term stability.

A fifth object of the present invention is to provide a silver halide photographic material which causes little change in activity during the production thereof and comprises emulsions having good long-term stability.

The above objects of the present invention have been achieved by a silver halide photographic material which comprises a support having thereon at least one hydrophilic colloid layer, wherein at least one hydrophilic colloid layer is a silver halide photographic emulsion layer, and at least one hydrophilic colloid layer contains a compound represented by the following general formula (I):

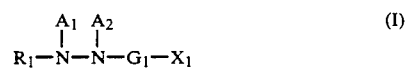

wherein $A_1$ and $A_2$ both represent a hydrogen atom, or one of $A_1$ and $A_2$ represents a hydrogen atom and the other represents a sulfonyl group or an acyl group; $R_1$ represents an aliphatic group or an aromatic group; $G_1$ represents a carbonyl group, a sulfonyl group, a sulfoxy group, a group of the formula

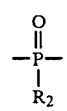

(wherein $R_2$ is an alkoxy group or an aryloxy group), a group of the formula

or an iminomethylene group; $X_1$ represents a residue of a nitrogen-containing heterocyclic ring; and at least one of $R_1$ and $X_2$ has an adsorption-accelerating group on silver halide.

DETAILED DESCRIPTION OF THE INVENTION

The compound represented by the formula (I) is illustrated in more detail below.

In the formula (I), $A_1$ and $A_2$ each represents a hydrogen atom, an alkylsulfonyl group having not more than 20 carbon atoms, an arylsulfonyl group (preferably a phenylsulfonyl group or a substituted phenylsulfonyl group which is substituted so that the sum of Hammett's substituent constants is −0.5 or more), an acyl group having not more than 20 carbon atoms (preferably a benzoyl group or a substituted benzoyl group which is substituted so that the sum of Hammett's substituent constants is −0.5 or more), or a straight-chain, branched or cyclic unsubstituted or substituted aliphatic acyl group (examples of substituent groups include a halogen atom, an ether group, a sulfonamido group, a carbonamido group, a hydroxyl group, a carboxyl group and a sulfonic acid group), provided that at least one of $A_1$ and $A_2$ is a hydrogen. The compounds where both $A_1$ and $A_2$ are a hydrogen atom, are most preferred.

The aliphatic group represented by $R_1$ is a straight-chain, branched or cyclic alkyl, alkenyl or alkynyl group. Those having 1 to 30 carbon atoms are preferred and those having 1 to 20 carbon atoms are particularly preferred. The branched alkyl group may be cyclized to form a saturated heterocyclic ring having one or more hetero-atoms.

Examples of the aliphatic group include a methyl group, a t-butyl group, an n-octyl group, a t-octyl group, a cyclohexyl group, a hexenyl group, a pyrrolidyl group, a tetrahydrofuryl group and an n-dodecyl group.

The aromatic group represented by $R_1$ is a monocyclic or bicyclic aryl group. Examples thereof include a phenyl group and a naphthyl group.

The group $R_1$ may be substituted by one or more substituent groups. Further, the substituent groups may be substituted.

Examples of the substituent groups include an alkyl group, an aralkyl group, an alkoxy group, an aryl group, a substituted amino group, an acylamino group, a sulfonylamino group, a ureido group, a urethane group, an aryloxy group, a sulfamoyl group, a carbamoyl group, an aryl group, an alkylthio group, an arylthio group, a sulfonyl group, a sulfinyl group, a hydroxyl group, a halogen atom, a cyano group, a sulfo group, and a carboxyl group.

These groups may be optionally combined together to form rings, if possible.

Preferably, $R_1$ is an aromatic group with an aryl group being particularly preferred.

$G_1$ is a carbonyl group, a sulfonyl group, a sulfoxy group, a group of the formula

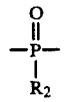

(wherein $R_2$ is an alkoxy group or an aryloxy group), a group of the formula

or an iminomethylene group.

The residue of a nitrogen-containing heterocyclic ring represented by $X_1$ in the formula (I) preferably represents a residue of a 5- or 6-membered nitrogen-containing heteroaromatic ring, which may be condensed with other rings. The specific examples include a pyridyl group, a pyrazinyl group, a pyrimidinyl group, a pyridazinyl group, a quinolyl group, an isoquinolyl group, a phthalazinyl group, a naphthyridinyl group, a quinoxalinyl group, a quinazolinyl group, a cynnolinyl group, a pteridinyl group or the like. These groups may be substituted. Examples of substituent groups include an alkyl group, an aryl group, a halogen atom, a substituted amino group, a cyano group, an acylamino group, a carboxyl group, an alkoxycarbonyl group, an aryloxycarbonyl group and combinations thereof.

At least one of $R_1$ and $X_1$ contains a group which accelerates adsorption on silver halide. The adsorption-accelerating group can be represented by $Y_1$−(−$L_2$−)$_l$ wherein $Y_1$ is an adsorption-accelerating group for silver halide, $L_2$ is a divalent linking group and $l$ is 0 or 1.

Preferred examples of the adsorption-accelerating group represented by $Y_1$ include a mercapto group, groups having a disulfide linkage and five-membered or six-membered nitrogen-containing heterocyclic groups.

The mercapto group represented by $Y_1$ may be an aliphatic mercapto group, an aromatic mercapto group or a heterocyclic mercapto group (when the atom next to the carbon atom to which −SH group is attached is a nitrogen atom, the group is the same as the cyclic thioamido group which exists in a tautomeric form with the mercapto group). Examples of these groups include a thioureido group, a thiourethane group, a dithiocarbamic ester group, etc. Examples of the cyclic thioamido group include 4-thiazoline-2-thione, 4-imidazoline-2-thione, 2-thiohydantoin, rhodanine, thiobarbituric acid, tetrazoline-5-thione, 1,2,4-triazoline-3-thione, 1,3,4-thiazoline-2-thione, 1,3,4-oxadiazoline-2-thione, benzimidazoline-2-thione, benzoxazoline-2-thione and benzthiazoline-2-thione. These groups may be further substituted.

The five-membered or six-membered nitrogen-containing heterocyclic groups represented by $Y_1$ include five-membered or six-membered nitrogen-containing heterocyclic groups consisting of combinations of nitrogen, oxygen, sulfur and carbon atoms. Among them, preferred examples include benzotriazole, triazole, tetrazole, indazole, imidazole, benzimidazole, benzthiazole, thiazole, benzoxazole, oxazole, thiadiazole, oxadiazole and triazine. These groups may be further substituted.

Examples of substituent groups include those already described above for R. Among the groups represented by $Y_1$, preferred groups are cyclic thioamido groups (namely, mercapto group-substituted nitrogen-containing heterocyclic groups such as 2-mercapto thiadiazole group, 3-mercapto-1,2,4-triazole group, 5-mercaptotetrazole group, 2-mercapto-1,3,4-oxadiazole group, 2-mercaptobenzoxazole group, etc.) and nitrogen-containing heterocyclic groups (e.g., benzotriazole group, benzimidazole group, indazole group, etc.).

Two or more groups $Y_1\text{-}(L_2)_l$ may be attached and these groups may be the same or different groups.

The divalent linking group represented by $L_2$ is an atom of C, N, S or O or an atomic group containing at least one atom selected from the group consisting of C, N, S and O. Examples of the group include an alkylene group, an alkenylene group, an alkynylene group, an arylene group, —O—, —S—, —NH—, —N=, —CO—, —SO$_2$—, etc. alone and combinations of two or more of them. These groups may be substituted.

More specific examples of these groups include —CONH—, —NHCONH—, —SO$_2$NH—, —COO—, —NHCOO—,

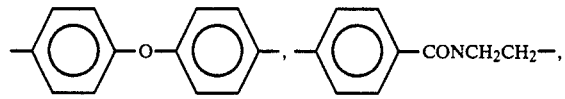

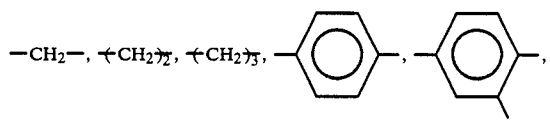

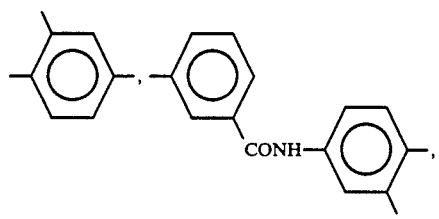

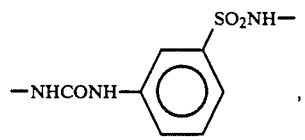

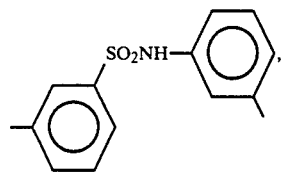

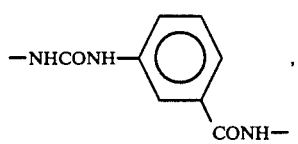

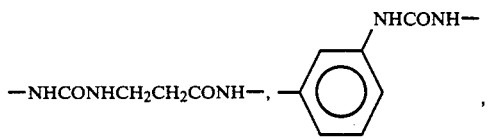

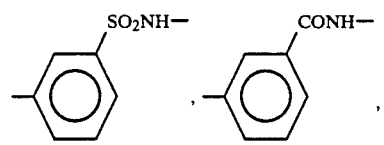

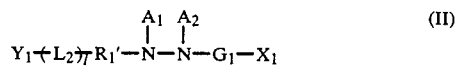

—CH$_2$CH$_2$SO$_2$NH—, —CH$_2$CH$_2$CONH—, etc.

These groups may be substituted by appropriate substituent groups. Examples of the substituent groups include those already described above for $R_1$.

Among the compounds represented by the formula (I), compounds represented by the following general formula (II) are preferred.

$$Y_1\text{-}(L_2)_l\text{-}R_1'-\overset{A_1}{\underset{|}{N}}-\overset{A_2}{\underset{|}{N}}-G_1-X_1 \quad (II)$$

In the above formula, $R_1'$ is a group formed by removing one hydrogen atom from $R_1$ in the formula (I); at least one of $R_1'$ and $L_2$ is a group which has a group capable of dissociating by an anion having a pKa of 6 or above and undergoes dissociation in the presence of an anion having a pKa of 6 or above, preferably a substituent group which undergoes dissociation in the presence of an anion having a pKa of 8 to 13. There may be used any substituent group without particular limitation, provided that the substituent group is hardly dissociated in neutral or weakly acidic mediums, but is sufficiently dissociated in aqueous alkaline solutions (preferably at a pH of 10.5 to 12.3) such as developing solutions.

Examples of such a group include a hydroxyl group, a group of —SO$_2$NH—, a hydroxyimino group (>C=N—OH), an active methylene group and an active methine group (e.g.,

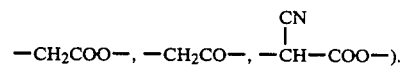

$A_1$, $A_2$, $G_1$, $X_1$, $Y_1$, $L_2$, and $l$ are the same as those set forth in the formula (1) and those already described above in the definition of the adsorption-accelerating group on silver halide.

Among the compounds represented by the formula (I), compounds represented by the following general formula (III) are particularly preferred.

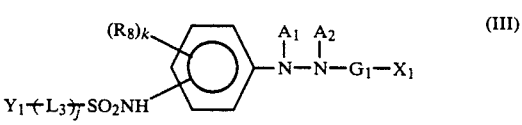

In the above formula, $R_8$ has the same meaning as $R_1$ in the formula (I); k is 0, 1 or 2; $L_3$ has the same meaning as $L_2$ in the formula (II); j is 0 or 1; and when k is 2, $R_8$ may be the same or different.

$A_1$, $A_2$, $G_1$, $X_1$ and $Y_1$ are the same as those set forth in the formulas (I) and (II).

More preferably are the compounds where $Y_1\text{-}(L_3)_j\text{-}SO_2NH$ group is attached at ortho- or para-position against hydrazino group.

Examples of the compounds represented by the formula (I) include, but are not limited to, the following compounds.

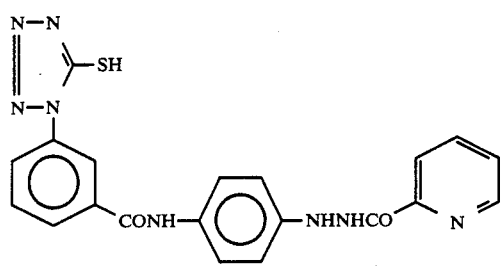
1-1)
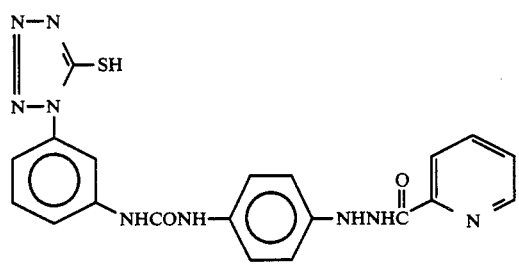
1-2)
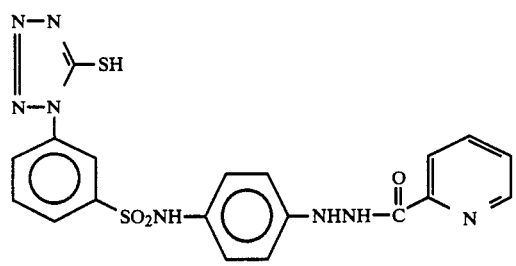
1-3)
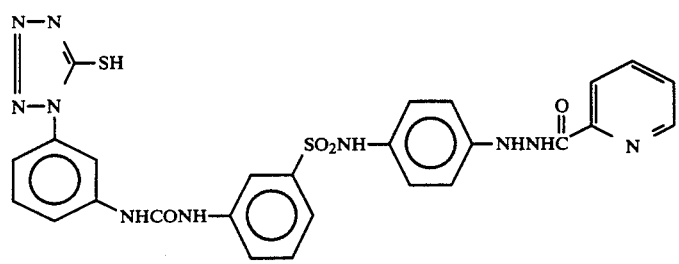
1-4)
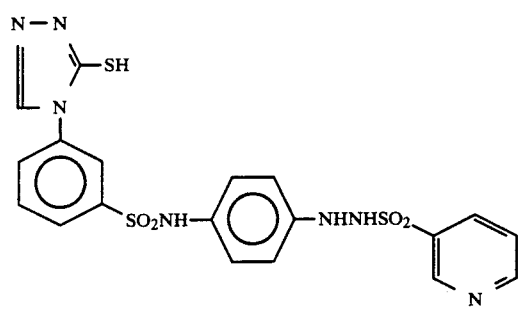
1-5)
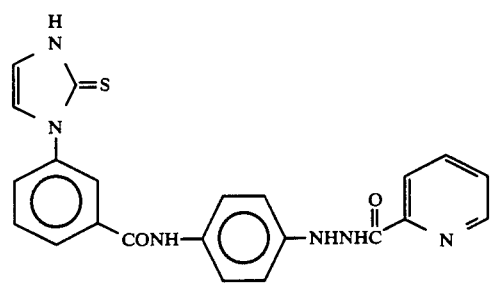
1-6)

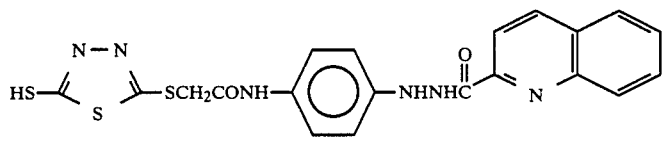
1-7)
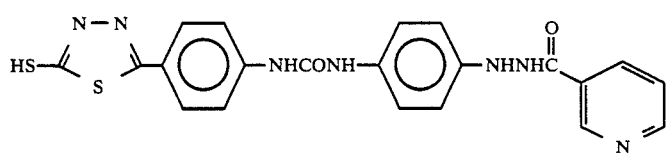
1-8)
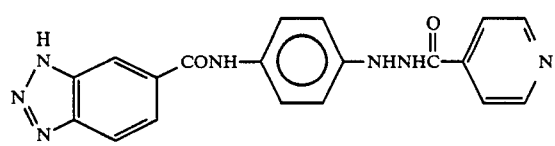
1-9)
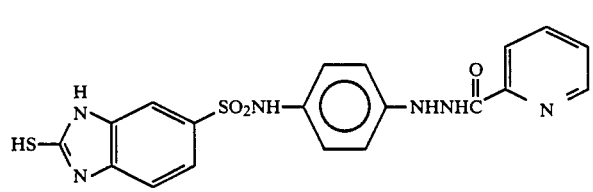
1-10)
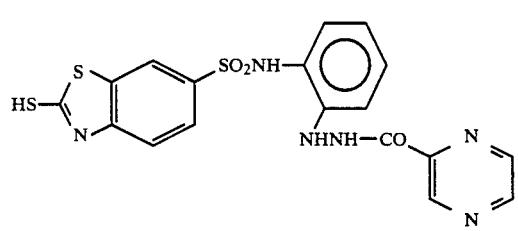
1-11)
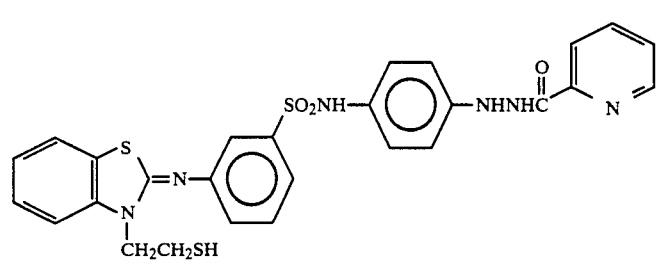
1-12)
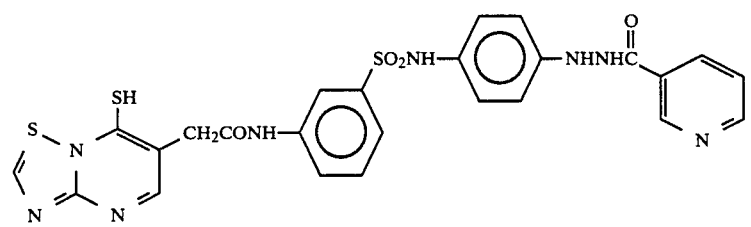
1-13)
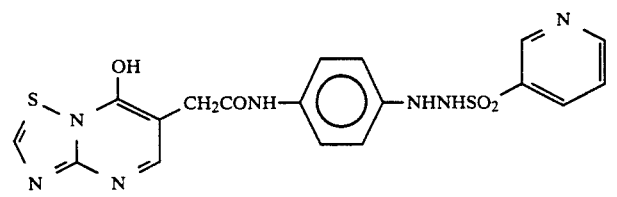
1-14)

-continued
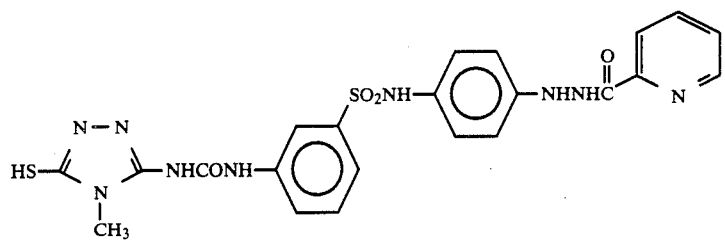
1-15)
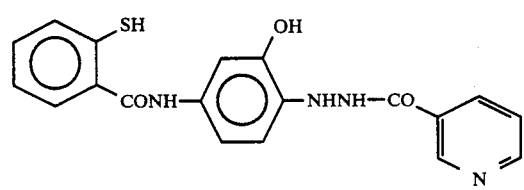
1-16)
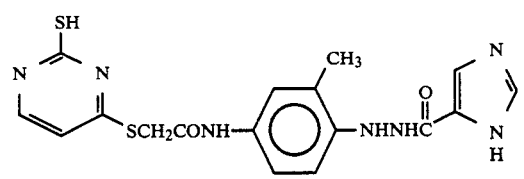
1-17)
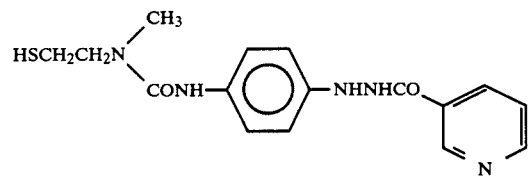
1-18)
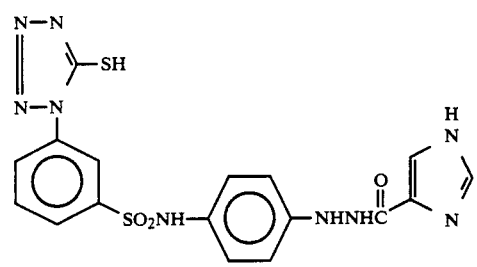
1-19)
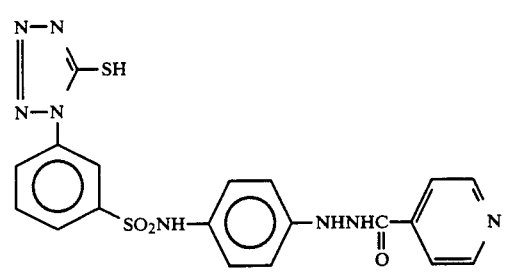
1-20)
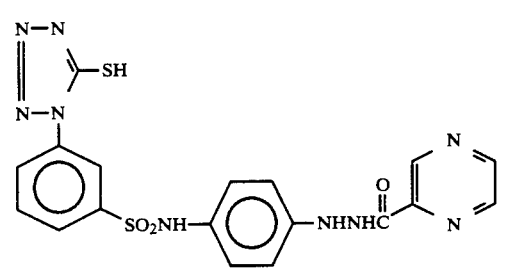
1-21)

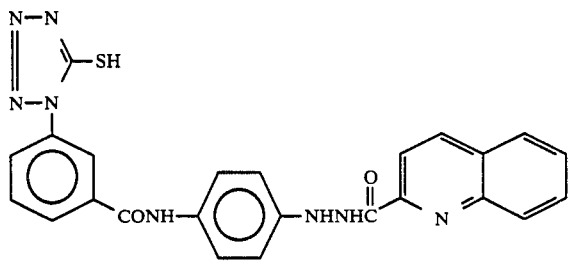

1-22)

The hydrazine derivatives of the present invention were synthesized by treating the corresponding known formylhydrazine compounds with hydrochloric acid and then reacting the treated products with the acid chloride of the desired nitrogen-containing heterocyclic carboxylic acids or sulfonic acid in the presence of pyridine.

Synthesis Example

Synthesis of compound I

Concentrated hydrochloric acid (4 ml) was added to a mixture of 7.2 g of the compound having the following formula

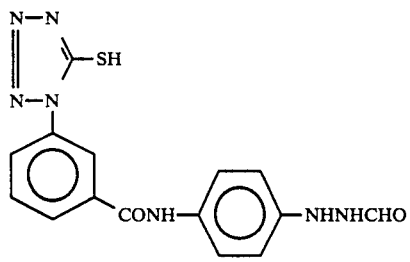

and methanol (50 ml). The mixture was stirred at room temperature overnight. After volatile matters were completely distilled off under reduced pressure, there were added acetonitrile (80 ml), DMF (dimethylformamide) (20 ml) and pyridine (10 ml). Thereafter, picolinic acid chloride hydrochloride (7.0 g) was added. The mixture was stirred at room temperature overnight and volatile matters were then distilled off under reduced pressure. The residue was purified by means of silica gel chromatography to obtain the desired product (yield: 2.1 g). NMR and IR spectra and elemental analysis confirm the chemical structure of this product.

Other compounds were also synthesized in the manner described above.

The compounds of the present invention can be incorporated in photographic emulsion layers and hydrophilic colloid layers by dissolving the compounds in water or water-miscible organic solvents (if desired, an alkali hydroxide or a tertiary amine may be added to form a salt which is then dissolved) and adding the resulting solution to hydrophilic colloid solutions (e.g., silver halide emulsion, aqueous gelatin solution)(if desired, pH may be adjusted by adding an acid or an alkali).

The compounds of the present invention may be used either alone or in a combination of two or more. The compounds of the present invention are used in an amount of preferably $1 \times 10^{-6}$ to $5 \times 10^{-2}$ mol, more preferably $1 \times 10^{-5}$ to $1 \times 10^{-2}$ mol per mol of silver halide. The amounts of the compounds to be used can be suitably chosen according to the properties of silver halide emulsions to be used in combination with the compounds.

The compounds having the formula (I) according to the present invention are preferably incorporated in photographic emulsion layers.

A high-contrast negative image can be formed when the compounds having the formula (I) according to the present invention are used in combination with negative type emulsions. Further, the compounds can be used in combination with internal latent image type silver halide emulsions. The compounds having the formula (I) can be utilized to form a high-contrast negative image by using them in combination with negative type emulsions.

When the compounds are used to form high-contrast negative image, it is preferred that silver halide to be used has a mean grain size in the range of fine grains (e.g., not larger than 0.7 μm, particularly preferably not larger than 0.5 μm). Though there are basically no limitations with regard to grain size distribution, monodisperse system is preferred. The term "monodisperse" as used herein means that at least 95% (by weight or in terms of the number of grains) of gains is composed of those having a grain size within ±40% of mean grain size.

Silver halide grains in the photographic emulsions may have regular crystal form such as cube, octahedron, rhombic dodecahedron or tetradecahedron, irregular crystal form such as sphere or tabular form or a composite form of those crystal forms.

The interior and surface layer of the silver halide grain may be composed of a uniform phase or of different phases.

Cadmium salt, sulfite, lead salt, thallium salt, rhodium salt or its complex salt, or iridium salt may be allowed to coexist during the formation of silver halide grains or during physical ripening in the preparation of the silver halide emulsions of the present invention.

The silver halide emulsions of the present invention may or may not be subjected to chemical sensitization. As methods for the chemical sensitization of the silver halide emulsions, there are known sulfur sensitization, reduction sensitization and noble metal sensitization. These methods may be used either alone or in combination to carry out chemical sensitization.

Typical noble metal sensitization is gold sensitization method using gold compounds, mainly gold complex. Noble metals such as complex salts of platinum, palladium and rhodium other than gold may be contained. Examples thereof are described in U.S. Pat. No. 2,448,060 and British Patent 618,016. Various sulfur compounds such as thiosulfates, thioureas, thiazoles and rhodanine in addition to sulfur compounds contained in gelatin can be used as the sulfur sensitizing agent.

It is preferred that iridium salt or rhodium salt is used before the completion of physical ripening, particularly during the formation of grains in the preparation of the silver halide emulsions.

It is preferred from the viewpoint of elevating maximum density (Dmax) that the silver halide emulsion layers of the present invention contain two kinds of monodispersed emulsions having different mean grain sizes as is described in JP-A-61-223734 and JP-A-62-90646. It is preferred that smaller-size monodispersed grains are chemically sensitized. Sulfur sensitization is most preferred as chemical sensitization. Larger-size monodispersed grains need not be chemically sensitized. However, the grains may be chemically sensitized. Since larger-size monodispersed grains are liable to form black peppers, the grains are generally not chemically sensitized. However, when chemical sensitization is carried out, it is particularly preferred that chemical sensitization is conducted only to such a slight extent that black peppers are not yet formed. The term "slight extent" as used herein means that chemical sensitization is carried out by shortening chemical sensitization time, lowering the temperature of chemical sensitization or reducing chemical sensitizing agents to be added in comparison with the chemical sensitization of smaller-size grains. Though there is no particular limitation with regard to a difference in sensitivity between a larger-size monodispersed emulsion and a smaller-size monodispersed emulsion, the difference is preferably 0.1 to 1.0, more preferably 0.2 to 0.7 in terms of $\Delta \log E$. It is preferred that the larger-size monodispersed emulsion has higher sensitivity than that of the smaller-size monodispersed emulsion. The sensitivity of each emulsion is one obtained by coating a support with the emulsion containing the hydrazine derivative and processing it with a developing solution having a pH of 10.5 to 12.3 and containing a sulfite ion at a concentration of at least 0.15 mol/l. The mean grain size of small-size monodispersed grains is not larger than 90%, preferably not larger than 80% of that of larger-size monodispersed grains. The mean grain size of silver halide emulsion grains is preferably 0.02 to 1.0 μm, more preferably 0.1 to 0.5 μm. It is preferred that the mean grain sizes of both the smaller-size and larger-size grains are in the range described above.

When two or more emulsions having different grain sizes are used in the present invention, the coating weight (in terms of silver) of smaller-size monodispersed emulsion is preferably 40 to 90 wt %, more preferably 50 to 80 wt % based on the total coating weight of silver.

In the present invention, monodispersed emulsions having different grain sizes may be introduced into the same emulsion layer or into separate layers. When they are introduced into separate layers, it is preferred that the larger-size emulsion is introduced into the upper layer and the smaller-size emulsion is introduced into the lower layer.

The total coating weight of silver is preferably 1 g/m² to 8 g/m².

Sensitizing dyes (e.g., cyanine dyes, merocyanine dyes, etc.) described in JP-A-55-52050 (pages 45 to 53) can be added to the photographic materials of the present invention to increase sensitivity. These sensitizing dyes may be used either alone or in combination. The combinations of the sensitizing dyes are often used for the purpose of supersensitization in particular. In addition to the sensitizing dyes, emulsions may contain a dye which itself does not have spectral sensitization effect, or a material which does not substantially absorb visible light but does exhibit supersensitizing activity. Useful sensitizing dyes, combinations of dyes for the purpose of supersensitization and materials exhibiting supersensitization are described in *Research Disclosure*, Vol. 176, No. 17643 (December, 1978), page 23, item IV-J.

The photographic materials may contain various compounds to prevent fogging from being caused during the manufacturing process and during storage of the photographic materials or during processing or to stabilize photographic performance. Namely, compounds known as antifogging agents or stabilizers such as azoles, for example, benzthiazolium salts, nitroindazoles, chlorobenzimidazoles, bromobenzimidazoles, mercaptothiazoles, mercaptobenzthiazoles, mercaptothiadiazoles, aminotriazoles, benzthiazoles and nitrobenzotriazoles; mercaptopyrimidines; mercaptotriazines; thioketo compounds, for example, oxazolinethione; azaindenes, for example, triazaindenes, tetraazaindenes (particularly, 4-hydroxy-substituted(1,3,3a,7)tetraazaindenes); pentaazaindenes; and benzenethiosulfonic acid, benzenesulfinic acid benzenesulfonamide can be added. Among them, benzotriazoles (e.g., 5-methyl benzotriazole) and nitroindazoles (e.g., 5-nitroindazole) are preferred. Alternatively, these compounds may be incorporated in processing solutions.

As development accelerators or accelerators for nucleating infectious development in the present invention, compounds described in JP-A-53-77616, JP A-54-37732, JP-A-53-137133, JP-A-60-140340 and JP-A-60-14959 and nitrogen- or sulfur-containing compounds can be effectively used.

The optimum amount of these acceralerators varies depending on the type of compound, but they are generally used in an amount of $1.0 \times 10^{-3}$ to 0.5 g/m², preferably $5.0 \times 10^{-3}$ to 0.1 g/m².

The photographic emulsion layers and other hydrophilic colloid layers of the photographic material of the present invention may contain desensitizers.

Organic desensitizers used in the present invention are determined by polarographic half wave potential, (namely, oxidation-reduction potential determined by polarography) and are those wherein the sum of the polarographic anode potential and cathode potential is positive A method for measuring oxidation-reduction potential by polarography is described in, for example, U.S. Pat. No. 3,501,307. It is preferred that the organic desensitizers have at least one water-soluble group such as a sulfonic acid group or a carboxyl group. These groups may form a salt with an organic base (e.g., ammonia, pyridine, triethylamine, piperidine, morpholine, etc.) or an alkali metal (e.g., sodium, potassium, etc.).

Preferable organic desensitizers used in the present invention include compounds represented by following formulae (IV) to (VI):

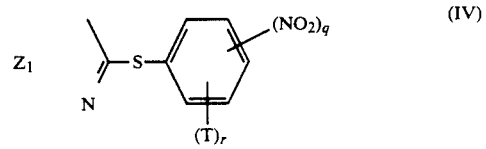

wherein T represents an alkyl group, a cycloalkyl group, an alkenyl group, a halogen atom, a cyano group, a trifluoromethyl group, an alkoxy group, an aryloxy group, a hydroxy group, an alkoxycarbonyl group, a carboxyl group, a carbamoyl group, a sulfamoyl group, an aryl group, an acylamino group, a sulfonamido group, a sulfo group or a benzocondensed ring, which may or may not have one or more substituents; $Z_1$ represents a group of nonmetal atoms required to complete a nitrogen-containing heterocyclic ring, which may or may not have one or more substituents; q is 1, 2 or 3; and r is 0, 1 or 2.

Specific examples of nitrogen-containing heterocyclic rings completed through $Z_1$ include a 1,2,4-triazole ring, a 1,3,4-oxidiazole ring, a 1,3,4-thiadiazole ring, a tetraazaindene ring, a pentaazaindene ring, a triazaindene ring, a benzothiazole ring, a benzimidazole ring, a benzoxazole ring, a pyrimidine ring, a triazine ring, a pyridine ring, a quinoline ring, a quinazoline ring, a phthalazine ring, a quinoxaline ring, an imidazo[4,5-b]quinoxaline ring, a tetrazole ring and a 1,3-diazaazulene ring, which may or may not have one or more substituents or may be fused with one or more additional aromatic rings.

Formula (V) is as follows:

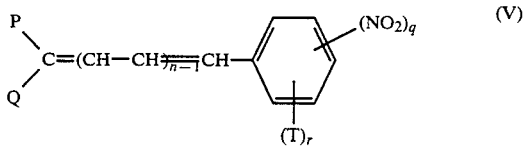

wherein P and Q, which may be the same or different, each represents a cyano group, an acyl group, a thioacyl group, an alkoxycarbonyl group, an alkylsulfonyl group, an arylsulfonyl group, a substituted or unsubstituted sulfamoyl group, a substituted or unsubstituted carbamoyl group, a nitro group, or a substituted or unsubstituted aryl group; n is 1, 2 or 3; and T, r and q have the same meaning as defined in formula (IV) above; and formula (VI) is as follows:

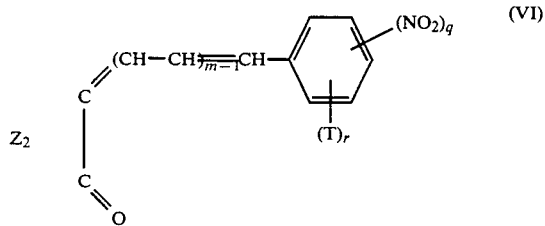

wherein $Z_2$ represents a group of nonmetal atoms required to complete a ketomethylene ring; m is 1, 2 or 3; and T, r and q have the same meaning as defined in formula (IV) above.

Specific examples of ketomethylene rings completed through $Z_2$ include a pyrazolone ring, an isoxazolone ring, an oxindol ring, a barbituric ring, a thiobarbituric ring, a rhodanine ring, an imidazo[1,2a]pyridone ring, a 2-thio-2,4-oxazolidinedione ring, a 2-thio-2,5-thiazolidinedione ring, a thiazolidone ring, a 4-thiazolone ring, a 2-imino-2,4-oxazolinone ring, a 2,4-imidazolinedione ring (a hydantoin ring), a 2-thiohydantoin ring and a 5-imidazolone ring.

The organic desensitizers are allowed to exist in an amount of $1.0 \times 10^{-8}$ to $1.0 \times 10^{-4}$ mol/m$^2$, particularly preferably $1.0 \times 10^{-7}$ to $1.0 \times 10^{-5}$ mol/m$^2$, in the silver halide emulsion of the present invention.

The emulsion layers and other hydrophilic colloid layers of the present invention may contain water-soluble dyes as filter dyes or for the purposes of irradiation prevention, etc. As the filter dyes, there are used dyes for lowering photographic sensitivity, preferably ultraviolet absorbers having a spectral absorption maximum in the region of sensitivity inherent in silver halide or dyes having light absorption in the region of mainly 380 nm to 600 nm to enhance safety to safelight in handling the photographic material as a daylight material.

Preferably, these dyes are added to the emulsion layers, or these dyes together with a mordant are added to the area above the silver halide emulsion layers. In other words, the dyes and the mordant are added to the light-insensitive hydrophilic colloid layer which is farther away from the support than the silver halide emulsion layer. After such addition the dyes are fixed.

The amounts of the dyes to be used vary depending on the molar absorption coefficient of the ultraviolet light absorber, but the dyes are generally used in an amount of $10^{-2}$ to 1 g/m$^2$, preferably 50 to 500 mg/m$^2$.

The above-described ultraviolet light absorbers are dissolved in an appropriate solvent [e.g., water, alcohol (e.g., methanol, ethanol, propanol, etc.), acetone, methyl cellosolve, etc. or a mixture thereof] and are then added to coating solutions.

As the ultraviolet light absorbers, there can be used aryl group-substituted benzotriazole compounds, 4-thiazolidone compounds, benzophenone compounds, cinnamic ester compounds, butadiene compounds, benzoxazole compounds and ultraviolet light absorbing polymers.

Examples of the ultraviolet light absorbers are described in U.S. Pat. Nos. 3,533,794, 3,314,794 and 3,352,681, JP-A-46-2784, U.S. Pat. Nos. 3,705,805, 3,707,375, 4,045,229, 3,700,455 and 3,499,762 and West German Patent Publication No. 1,547,863.

Examples of the filter dyes include oxonol dyes, hemioxonol dyes, styryl dyes, merocyanine dyes, cyanine dyes and azo dyes. Water-soluble dyes or dyes which can be decolorized by alkalis or sulfite ions are preferred from the viewpoint of reducing the formation of aftercolor after developing.

Examples of the dyes include pyrazolone oxonol dyes described in U.S. Pat. No. 2,274,782; diaryl azo dyes described in U.S. Pat. No. 2,956,879; styryl dyes and butadiene dyes described in U.S. Pat. Nos. 3,423,207 and 3,384,487; merocyanine dyes described in U.S. Pat. No. 2,527,583; merocyanine dyes and oxonol dyes described in U.S. Pat. Nos. 3,486,897, 3,652,284 and 3,718,472; enaminohemioxonol dyes described in U.S. Pat. No. 3,976,661; and dyes described in British Patents 584,609 and 1,177,429, JP-A-48-85130, JP-A-49-99620, JP-A-49-114420, U.S. Pat. Nos. 2,533,472, 3,148,187, 3,177,078, 3,247,127, 3,540,887, 3,575,704 and 3,653,905.

The dyes are dissolved in an appropriate solvent [e.g., water, alcohol (e.g., methanol, ethanol, propanol, etc.), acetone, methyl cellosolve, etc. or a mixture thereof] and are then added to coating solutions for the light-insensitive hydrophilic colloid layers of the present invention.

Specifically, the dyes are used in an amount of generally $10^{-3}$ to 1 g/m$^2$, particularly preferably $10^{-3}$ to 0.5 g/m$^2$.

The photographic emulsion layers and other hydrophilic colloid layers of the photographic material of the present invention may contain inorganic or organic hardening agents such as chromium salts, aldehydes (e.g., formaldehyde, glutaraldehyde, etc.), N-methylol compounds (e.g., dimethylol urea), active vinyl compounds (e.g., 1,3,5-triacryloyl-hexahydro-s-triazine, 1,3-vinylsulfonyl-2-propanol), active halogen compounds (e.g., 2,4-dichloro-6-hydroxy-s-triazine), mucohalogen acids, etc. These compounds may be used either alone or in combination.

The photographic emulsion layers or other hydrophilic colloid layers of the photographic material of the present invention may contain surfactants as a coating aid or to impart antistatic properties, improve sliding properties and emulsified dispersion, prevent adhesion or improve photographic characteristics (e.g., development acceleration, sensitization, high contrast). Particularly preferred examples of surfactants which can be used in the present invention are polyalkylene oxides having an molecular weight of not less than 600 which are described in JP-B-58-9412 (the term "JP B" as used herein means an "an examined Japanese patent application"). When the surfactants are to be used as antistatic agents, fluorine-containing surfactants (in detail described in U.S. Pat. No. 4,201,586, JP-A-60-80849, JP-A-59-74554) are particularly preferred.

The photographic emulsion layers and other hydrophilic colloid layers of the photographic material of the present invention may contain a matting agent such as silica, magnesium oxide, polymethyl methacrylate to prevent adhesion.

The photographic emulsions of the present invention may contain a dispersion of a water-insoluble or sparingly water-soluble synthetic polymer to improve dimensional stability. For this purpose, there can be used, for example, polymers of alkyl (meth)acrylates, alkoxyalkyl (meth)acrylates, glycidyl (meth)acrylates, etc., singly or a mixture thereof, or copolymers thereof with a monomer component such as acrylic acid or methacrylic acid.

It is preferred that the silver halide emulsion layers and other layers of the photographic material of the present invention contain a compound having an acid group. Examples of compounds having an acid group include organic acids such as salicylic acid, acetic acid and ascorbic acid and polymers having a repeating unit of an acid monomer such as acrylic acid, maleic acid, phthalic acid or the like or copolymers of these monomers. These compounds are described in JP-A-61-223834, JP-A-61-228437, JP-A-62-25745 and JP-A-62-55642. Among them, a particularly preferred low-molecular compound is ascorbic acid. There are particularly preferred water-dispersible latexes of copolymers of an acid monomer such as acrylic acid with a crosslinking monomer having two or more unsaturated groups such as divinyl benzene as high-molecular weight compounds.

Stable developing solutions can be used to obtain superhigh-contrast, high-sensitivity photographic characteristics by using the silver halide photographic material of the present invention without using conventional infectious developing solutions or highly alkaline developing solutions having a pH near 13 described in U.S. Pat. No. 2,419,975.

The silver halide photographic materials of the present invention give sufficiently superhigh-contrast negative image by using developing solutions having a pH of 10.5 to 12.3, particularly 11.0 to 12.0 and containing a sulfite ion as preservative at a concentration of not less than 0.15 mol/l.

Though there are no particular limitations with respect to developing agents used in the developing solutions of the present invention, it is preferred from the viewpoint of easily obtaining halftone dots of good quality that dihydroxybenzenes are present. Combinations of dihydroxybenzenes and 1-phenyl-3-pyrazolidones or combinations of dihydroxybenzenes and p-aminophenols are also used. The developing agents are used in an amount of preferably 0.05 to 0.8 mol/l. When combinations of dihydroxybenzenes and 1-phenyl-3-pyrazolidones or p-aminophenols are used, the former is used in an amount of 0.05 to 0.5 mol/l and the latter is used in an amount of preferably not more than 0.06 mol/l.

Sulfite preservatives which are used in the present invention include sodium sulfite, potassium sulfite, lithium sulfite, ammonium sulfite, sodium bisulfite, potassium metabisulfite and formaldehydesodium bisulfite. The sulfites are used in an amount of not less than 0.4 mol/l, particularly preferably not less than 0.5 mol/l.

Compounds described in JP-A-56-24347 can be used as silver stain inhibitors in the developing solutions of the present invention. Compounds described in JP-A-61-267759 can be used as dissolution aids to be added to the developing solutions. Compounds described in JP-A-60-93433 or JP-A-62-186259 can be used as pH buffer agents to be used for the developing solutions.

Specific examples of the silver stain inhibitors are as follows.

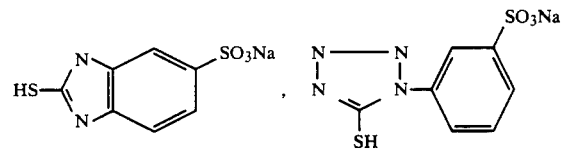

Specific examples of the dissolution aid include p-toluene sulphonic acid sodium salt, and specific examples of the pH buffer agents include borate, 5-sulfosalicylic acid and phosphate.

The compounds of the formula (I) can be used in combination with negative type emulsions to give high-contrast photographic materials as described above. In addition thereto, the compounds can be used in combination with internal latent image type silver halide emulsions. Embodiments therefor are illustrated below. It is preferred that the compounds having the formula (I) are incorporated in the internal latent image type silver halide emulsion layers. However, the compounds may be incorporated in hydrophilic colloid layers adjacent to the internal latent image type silver halide emulsion layers. Such layers include a coloring material layer, an interlayer, a filter layer, a protective layer and an antihalation layer. The layers may be those having any function, so long as interference with the diffusion of the nucleating agents in silver halide grains does not occur.

It is desirable that the contents of the compounds having the formula (I) in the layers are in an amount to give sufficient maximum density (e.g., at least 1.0 in terms of silver density) when the internal latent image type emulsions are developed with surface developing solutions. Practically, the contents vary depending on the characteristics of the silver halide emulsions to be used, the chemical structures of the nucleating agents and developing conditions. Hence, suitable contents vary widely, but the contents of the compounds are practically in the range of about 0.005 mg to 500 mg per mol of silver in the internal latent image type silver halide emulsion, preferably in the range of about 0.01 mg to about 100 mg per mol of silver. When the compounds are to be incorporated in the hydrophilic colloid layers adjacent to the emulsion layers, the same amount as that described above in connection with the amount of silver contained in the same area as that of the internal latent image type emulsion layer may be incorporated. The definition of the internal latent image type silver halide emulsion is described in JP-A-61-170733 (page 10, upper column) and British Patent 2,089,057 (pages 18 to 20).

Preferred internal latent image type emulsions which can be used in the present invention are described in JP-A-63-108336 (page 28, line 14 to page 31, line 2) which corresponds to European Patent Application 267482A and preferred silver halide grains are described in JP-A-63-108336 (page 31, line 3 to page 32, line 11).

The internal latent image type emulsions of the photographic material of the present invention may be spectral-sensitized to relatively long-wave blue light, green light, red light or infrared light by using sensitizing dyes. Examples of the sensitizing dyes which can be used include cyanine dyes, merocyanine dyes, complex cyanine dyes, complex merocyanine dyes, holopolar cyanine dyes, styryl dyes, hemicyanine dyes, oxonol dyes and hemioxonol dyes. Cyanine dyes and merocyanine dyes described in JP-A-59-40638, JP-A-59-40636 and JP-A-59-38739 are included in these sensitizing dyes.

Dye image forming couplers can be incorporated as coloring materials in the photographic material of the present invention. Alternatively, development may be carried out with developing solutions containing dye image forming couplers.

Examples of cyan, magenta and yellow couplers which can be used in the present invention are described in patents cited in *Research Disclosure* (RD), No. 17643 (December, 1978), item VII-D and ibid., No. 18717 (November, 1979).

There can be used couplers giving color forming dyes which are properly diffusing, non-color forming couplers, DIR couplers releasing a development restrainer by a coupling reaction, and couplers releasing a development accelerator.

Typical examples of yellow couplers which can be used in the present invention are the oil protect type acylacetamide couplers.

Two equivalent type yellow couplers are preferably used in the present invention. Typical examples thereof are the oxygen atom elimination type yellow couplers and the nitrogen atom elimination type yellow couplers. α-Pivaloylacetanilide couplers give color dyes which are excellent in fastness, particularly fastness to light, and o-benzoylacetanilide couplers give high color density.

Examples of magenta couplers which can be used in the present invention include oil protect type indazolone couplers, cyanoacetyl couplers, preferably 5-pyrazolone couplers and pyrazoloazole couplers such as pyrazolotriazole. 5-Pyrazolone couplers having an arylamino group or an acylamino group at the 3-position are preferred from the viewpoint of the hue and color density of the color forming dyes. Nitrogen atom elimination groups described in U.S. Pat. No. 4,310,619 and arylthio groups described in U.S. Pat. No. 4,351,897 are preferred as the elimination groups of two equivalent type 5-pyrazolone couplers. 5-Pyrazolone couplers having a ballast group described in European Patent 73,636 give high color density.

Examples of the pyrazoloazole couplers include pyrazolobenzimidazoles described in U.S. Pat. No. 3,379,899, preferably pyrazolo[5,1-c][1,2,4]triazoles described in U.S. Pat. No. 3,725,067, pyrazolotetrazoles described in *Research Disclosure*, No. 24220 (June, 1984) and pyrazolopyrazoles described in *Research Disclosure*, No. 24230 (June, 1984). Imidazo[1,2-b]pyrazoles described in European Patent 119,741 are preferred from the viewpoint of fastness to light and less secondary absorption of yellow of formed color dyes, and pyrazolo[1,5-b][1,2,4]triazole described in European Patent 119,860 is particularly preferred.

Cyan couplers which can be used in the present invention include oil protect type naphthol couplers and phenol couplers. Typical examples of the naphthol couplers include naphthol couplers described in U.S. Pat. No. 2,474,293 and preferably oxygen atom elimination type two equivalent type naphthol couplers described in U.S. Pat. Nos. 4,052,212, 4,146,396, 4,228,233 and 4,296,200. Examples of the phenol couplers include those described in U.S. Pat. Nos. 2,369,929, 2,801,171, 2,772,162 and 2,895,826. Cyan couplers having fastness to moisture and heat are preferably used in the present invention. Typical examples thereof include phenol cyan couplers having an ethyl group or a higher alkyl group at the meta-position of the phenol nucleus, 2,5-diacylamino-substituted phenol couplers and phenol couplers having a phenylureido group at the 2-position and acylamino group at the 5-position described in U.S. Pat. No. 3,772,002.

It is preferred that colored couplers in combination with the above couplers are used in color photographic materials for photographing to correct unnecessary absorption in the region of short wave for dyes formed from magenta and cyan couplers.

Couplers giving color dyes which are properly diffusing can be used to improve graininess. Such dye-diffusing couplers include magenta couplers described in U.S. Pat. No. 4,366,237 and British Patent 2,125,570 and yellow, magenta or cyan couplers described in European Patent 96,570 and West German Patent Application (OPI) No. 3,234,533.

The dye forming couplers and the above-described specific couplers may be in the form of a dimer or higher polymer. Typical examples of the dye forming polymer couplers are described in U.S. Pat. Nos. 3,451,820 and 4,080,211. Examples of magenta polymer couplers are described in British Patent 2,102,173 and U.S. Pat. No. 4,367,282.

Various kinds of couplers which are used in the present invention may be used in such a manner that two or more kinds of couplers in combination may be used for the same layer of the photographic layers, or the same compound may be introduced into two or more different layers to meet requirements of characteristics required for the photographic materials.

The color couplers are generally used in an amount of 0.001 to 1 mol per mol of sensitive silver halide. Yellow couplers are used in an amount of 0.01 to 0.5 mol, magenta couplers are used in an amount of 0.003 to 0.3 mol, and cyan couplers are used in an amount of 0.002 to 0.3 mol.

In the present invention, developing agents such as hydroxybenzenes (e.g., hydroquinone), aminophenols and 3-pyrazolidones may be incorporated in emulsions or photographic materials.

Photographic emulsions which are used in the present invention can be used in combination with dye image donating compounds (coloring materials) for color diffusion transfer process, said compounds releasing diffusing dye corresponding to the development of silver halide, to obtain a desired transferred image on an image receiving layer after appropriate development processing. Many coloring materials for color diffusion transfer process are known. Among them, there are preferred coloring materials (hereinafter referred to as DRR compound) which are initially nondiffusing, but are cleaved by the oxidation-reduction reaction with the oxidation products of developing agents (or electron transfer agents) to release diffusing dyes. Among them, DRR compounds having N-substituted sulfamoyl group are preferred. Particularly preferred DRR compounds suitable for use in combination with the nucleating agents of the present invention are the DRR compounds having o-hydroxyarylsulfamoyl group described in U.S. Pat. Nos. 4,055,428, 4,053,312 and 4,336,322 and the DRR compounds having redox parent nucleus described in JP-A-53-149328. When used in combination with such DRR compounds, temperature dependence during processing in particular is remarkably low.

Examples of the DRR compounds in addition to those described in the above-mentioned patent specifications include magenta dye image forming materials such as 1-hydroxy-2-tetramethylenesulfamoyl-4-[3'-methyl-4'-(2''-hydroxy-4''-methyl-5''-hexadecyloxy-phenylsulfamoyl)phenylazo]-naphthalene and yellow dye image forming materials such as 1-phenyl-3-cyano-4-(2''',4'''di-tertpentylphenoxyacetamino)-phenylsulfamoyl]phenylazo)-5-pyrazolone.

It is preferred that after the photographic material of the present invention is imagewise exposed, direct positive color image is formed by (1) carrying out color development with surface developing solutions having a pH of not higher than 11.5 and containing aromatic primary amine color developing agents and (2) conducting bleaching-fixing treatment after or while fogging treatment is carried out by light or nucleating agents. It is more preferred that the pH of the developing solutions is in the range of 11.0 to 10.0.

The fogging treatment of the present invention may be carried out by a so-called light fogging method wherein a second exposure is applied to the whole surface of light-sensitive layer or by a so-called chemical fogging method wherein development is carried out in the presence of a nucleating agent. If desired, development may be conducted in the presence of a nucleating agent and fogging light, or a photographic material containing a nucleating agent may be subjected to fogging exposure.

The light fogging method is described in the aforesaid JP-A-63-108336 (page 47 line 4 to page 49 line 5). Nucleating agents which can be used in the present invention are described in JP-A-63-108336 (page 49 line 6 to page 67 line 2). The compounds represented by the formulas [N-1] and [N-2] are particularly preferred. Preferred examples of these compounds are the following compounds.

(N-I-1): 6-ethoxy-2-methyl-1-propargylquinolinium bromide
(N-I-2): 2,4-dimethyl-1-propargylquinolinium bromide
(N-I-3) 2-methyl-1-{3-[2-(4-methylphenyl)hydrazono]-butyl}quinolinium iodide
(N-I-4): 3,4-dimethyl-dihydropyrido[2,1-b]benzothiazolium bromide
(N-I-5): 6-ethoxythiocarbonylamino-2-methyl-1-propargyl-quinolinium trifluoromethanesulfonate
(N-I-6): 2-methyl-6-(3-phenylthioureido)-1-propargyl-quinolium bromide
(N-I-7): 6-(5-benzotriazolocarboxyamido)-2-methyl-1-propargylquinolinium trifluoromethane sulfonate
(N-I-8): 6-[3-(2-mercaptoethyl)ureido]-2-methyl-1-propargylquinolinium trifluoromethane-sulfonate
(N-I-9): 6-{3-[3-(5-mercapto-thiadiazolo-2-ylthio)-propyl]-ureido -2-methyl-1-propargylquinolinium} tri-fluoromethanesulfonate
(N-I-10): 6-(5-mercaptotetrazolo-1-yl)-2-methyl-1-propargylquinolinium iodide
(N-II-1): 1-formyl-2-{4-[3-(2-methoxyphenyl)ureido]-phenyl}hydrazine
(N-II 2): 1-formyl-2-{4-[3-{3-[3-(2,4-di-tert-pentylphenoxy)propyl]ureido}phenylsulfonylamino]phenyl} hydrazine
(N-II-3): 1-formyl-2-{4-[3-(5-mercaptotetrazolo-1-yl)benzamido]phenyl}hydrazine
(N-II-4): 1-formyl-2-[4-{3-[3-(5-mercaptotetrazolo-1-yl)-phenyl]ureido}phenyl]hydrazine
(N-II-5): 1-fromyl-2-[4-{3-[N-(5-mercapto-4-methyl-1,2,4-triazolo-3-yl)carbamoyl]propaneamido} phenyl]-hydrazine
(N-II-6): 1-formyl-2-{4-[3-{N-[4-(3-mercapto-1,2,4-triazolo-4-yl)phenyl]carbamoyl}propaneamido]-phenyl}hydrazine
(N-II-7): 1-formyl-2-[4-{3-[N-(5-mercapto-1,3,4-thiadiazolo-2-yl)carbamoyl]propaneamido}phenyl]-hydrazine
(N-II-8): 2-[4-(benzotriazolo-5-carboxamido)-phenyl]-1-formylhydrazine
(N-II-9): 2-[4-{3-[N-benzotriazolo-5-carboxamido)carbamoyl]propaneamido}phenyl]-1-formylhydrazine
(N-II-10): 1-formyl-2-{4-[1-(N-phenylcarbamoyl)thiosemi-carbazido]phenyl}hydrazine
(N-II-11): 1-formyl-2-{4-[3-(phenylthioureido)benzamido]-phenyl}hydrazine
(N-II-12): 1-formyl-2-[4-{3-hexylureido)phenyl]hydrazine Nucleation accelerators which can be used in the present invention are described in JP-A-63-108336 (page 68, line 11 to page 71, line 3). Preferred examples thereof are the compounds represented by (A-1) to (A-13) described in JP-A-63-108336 (pages 69 to 70).

Color developing solutions which can be used in the development of the photographic material of the present invention are described in JP-A-63-108336 (page 71, line 4 to page 72, line 9). Particularly preferred examples of aromatic primary amine color developing agents include p-phenylenediamine compounds. Typical examples thereof include 3-methyl-4-amino-N-ethyl-N-($\beta$-methanesulfonamidoethyl)aniline, 3-methyl-4-amino-N-ethyl-N-($\beta$-hydroxyethyl)aniline, 3-methyl-4-amino-N-ethyl-N-methoxyethylaniline and salts thereof such as sulfate and hydrochloride.

In addition to the above color developing agents, black-and-white developing agents such as phenidone derivatives can be used to form direct positive color image by a color diffusion transfer process using the photographic material of the present invention.

After color development, the photographic emulsion layers are generally bleached. Bleaching and fixing may be carried out simultaneously with one bath for bleaching-fixing treatment, or they may be separately carried out. After bleaching, a bleaching-fixing treatment may be conducted to expedite processing. After fixing, a bleaching-fixing treatment may be carried out. Generally, iron complex salts of aminopolycarboxylic acids are used as bleaching agents for the bleaching solution or bleaching-fixing solution of the present invention. The bleaching solution or bleaching-fixing solution of the present invention may contain additives. For example, compounds described in JP-A-62-215272 (pages 22 to 30) can be used as the additives. After desilverization (bleaching-fixing or fixing), rinsing and/or stabilization are/is carried out. Preferably, softened water is used for rinsing water or stabilizing solution. Examples of methods for softening water include methods using ion exchange resins or reverse osmosis device described in JP-A-62-288838. Concretely, these methods are preferably carried out according to the methods described in JP-A-62-288838.

Compounds described in JP-A-62-215272 (pages 30 to 36) can be used as additives for the rinsing stage and the stabilization stage.

It is preferred that the amount of replenisher in each stage is as possible as small. The amount of the replenisher per unit area of photographic material is preferably 0.1 to 50 times, more preferably 3 to 30 times, the amount brought over from the previous bath.

The present invention is now illustrated in greater detail by reference to the following examples which, however, are not to be construed as limiting the invention in any way.

EXAMPLE 1

First, $4 \times 10^{-7}$ mol of potassium hexachloro iridate (III) per mol of silver, an aqueous solution of silver nitrate, and an aqueous solution of potassium iodide and potassium bromide in the presence of ammonia were simultaneously added to an aqueous gelatin solution kept at 50° C. over a period of 60 minutes while keeping a pAg value at 7.8, thus preparing a cubic monodispersed emulsion having a mean grain size of 0.28 μm and an average silver iodide content of 0.3 mol %.

The emulsion was desilverized by flocculation. Thereafter, 40 g (per mol of silver) of inactive gelatin was added thereto. The temperature of the emulsion was kept at 50° C., and 5,5'-dichloro-9-ethyl 3,3'-bis-(3-sulfopropyl)oxacarbocyanine as a sensitizing dye and $10^{-3}$ mol (per mol of silver) of KI solution were added thereto. After the lapse of 15 minutes, the temperature was lowered. The emulsion was re-dissolved. At 40° C., 0.02 mol (per mol of silver) of methylhydroquinone and the hydrazine derivative (shown in Table 1) of the present invention or Comparative Example were added thereto. Further, 5-methylbenztriazole, 4-hydroxy-1,3,3a,7-tetraazaindene, the following development accelerators (a) and (b), a dispersion of polyethyl acrylate in an amount 0.4 g/m² and the following compound (c) as a gelatin hardener were added to the emulsion. A polyethylene terephthalate support (150 μm) having a waterproof undercoat layer (0.5 μm) composed of a vinylidene chloride copolymer was coated with the emulsion in such an amount as to give a coating weight of 3.4 g/m² in terms of silver.

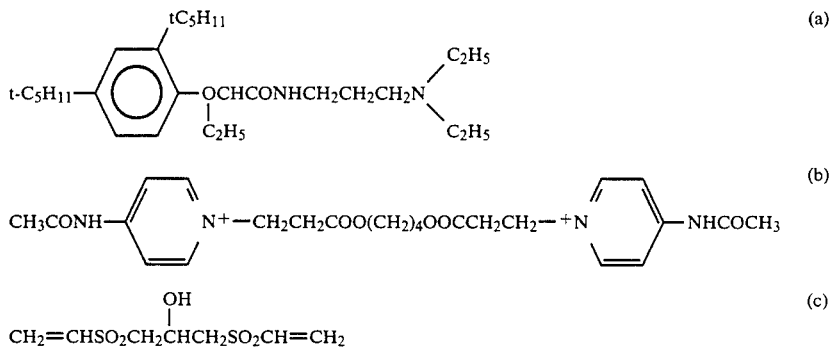

Further, a layer containing gelatin (1.5 g/m²), polymethyl methacrylate particles (average particle diameter: 2.5 μm, 0.3 g/m²) and the following surfactants as a protective layer was coated thereon.

| Surfactants | |
|---|---|
| 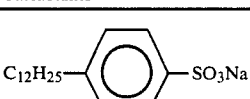 | 37 mg/m² |
| $CH_2COOC_6H_{13}$<br>\|<br>$CHCOOC_6H_{13}$<br>\|<br>$SO_3Na$ | 37 mg/m² |
| $C_8F_{17}SO_2NCH_2COOK$<br>\|<br>$C_3H_7$ | 2.5 mg/m² |

[1] Evaluation of High-Contrast Performance

These samples were exposed through an optical wedge by using tungsten lamp of 3200° K. The samples were developed with the following developing solution at 34° C. for 30 seconds, fixed with a fixer GR-F1 (made by Fuji Photo Film Co., Ltd.) at 30° C. for 30 seconds, washed with water for 30 seconds and dried at 45° C. for 20 seconds. Photographic sensitivity and gradation obtained are shown in Table 1. When the nucleating agents of the present invention were used, high sensitivity and higher high-contrast property could be obtained.

| Developing solution-I | |
|---|---|
| Hydroquinone | 50.0 g |
| N-Methyl-p-aminophenol | 0.3 g |
| Sodium hydroxide | 18.0 g |
| 5-Sulfosalicylic acid | 55.0 g |
| Potassium sulfite | 110.0 g |
| Disodium ethylenediaminetetraacetate | 1.0 g |
| Potassium bromide | 10.0 g |
| 5-Methylbenzotriazole | 0.4 g |

-continued

| Developing solution-I | |
|---|---|
| 2-Mercaptobenzimidazole-5-sulfonic acid | 0.3 g |
| Sodium 3-(5-mercaptotetrazole)-benzenesulfonate | 0.2 g |
| N-n-Butyldiethanolamine | 15.0 g |
| Sodium toluenesulfonate | 8.0 g |
| Water to make | 1 liter |
| Adjust pH to 11.6 (by adding potassium hydroxide) | pH 11.6 |

[2] Evaluation of Photographic Characteristics with Exhausted Developing Solution The above developing solution I was charged into automatic processor FG660F type (manufactured by Fuji Photo Film Co., Ltd.) for photomechanical process. Development was carried out under the following three conditions at 34° C. for 30 seconds, fixed with a fixer GR-F1 at 30° C. for 30 seconds, washed with water for 30 seconds and dried at 45° C. for 20 seconds.

[A] Development was carried out immediately after the temperature of the developing solution introduced into the automatic processor reached 34° C. (development with fresh solution).

[B] The developing solution was charged into the automatic processor and the solution as charged was left to stand for 4 days. Development was carried out with said solution (development) with air-exhausted solution).

[C] After the developing solution was charged into the automatic processor, GRANDEX GA-100 film (manufactured by Fuji Photo Film Co., Ltd.) (film size: 50.8 cm × 61.0 cm) was exposed so that the 50% area of the film was developed. Two hundred sheets per day were processed. Development was carried out with the solution which was repeatedly used for 5 days. One hundred cc of the developing solution I per one processed sheet was replenished. (development with exhausted solution used for mass-processing).

The resulting photographic characteristics are shown in Table 1. It is preferred from the viewpoint of process running stability that the photographic characteristics obtained by [B] or [C] are not different from those of [A]. It can be understood from the results of Table 1 that when the nucleating agents of the present invention are used, fluctuation in photographic sensitivity is hardly caused even when the developing solution is exhausted.

TABLE 1

| | Nucleating agent | | Photographic characteristics with fresh solution | | Change of photographic characteristics with exhausted solution | |
|---|---|---|---|---|---|---|
| | | | | | Air-exhausted solution | Exhausted solution used for mass-processing |
| Sample No. | Kind | Amount (mol/mol of Ag) | Sensitivity (S)* | Gradation (G)** | $(\Delta S_{B-A})$*** | $(\Delta S_{C-A})$**** |
| 1 Comp. Ex. | 1 blank | — | 0 | 3.0 | — | — |
| 2 Comp. Ex. | 2 Comparative compound A | $2.5 \times 10^{-4}$ | +0.42 | 12.1 | +0.23 | −0.21 |
| 3 Comp. Ex. | 3 Comparative compound B | " | +0.25 | 10.0 | +0.18 | −0.15 |
| 4 Comp. Ex. | 4 Comparative compound C | $5.0 \times 10^{-5}$ | +0.18 | 8.7 | +0.35 | −0.18 |
| 5 Invention | 1 Compound I-1 | " | +0.45 | 12.5 | +0.16 | −0.10 |
| 6 Invention | 2 Compound I-2 | " | +0.48 | 14.3 | +0.14 | −0.09 |
| 7 Invention | 3 Compound I-3 | " | +0.51 | 17.4 | +0.10 | −0.07 |
| 8 Invention | 4 Compound I-4 | " | +0.53 | 17.9 | +0.09 | −0.07 |
| 9 Invention | 5 Compound I-9 | " | +0.41 | 13.0 | +0.15 | −0.13 |
| 10 Invention | 6 Compound I-19 | " | +0.47 | 16.8 | +0.10 | −0.07 |
| 11 Invention | 7 Compound I-20 | " | +0.29 | 17.0 | +0.09 | −0.07 |

TABLE 1-continued

| Sample No. | Nucleating agent Kind | Amount (mol/mol of Ag) | Photographic characteristics with fresh solution Sensitivity (S)* | Gradation (G)** | Change of photographic characteristics with exhausted solution Air-exhausted solution $(\Delta S_{B-A})$*** | Exhausted solution used for mass-processing $(\Delta S_{C-A})$**** |
|---|---|---|---|---|---|---|
| 12 Invention | 8 Compound I-21 | " | +0.32 | 16.9 | +0.09 | −0.08 |

[Comparative compound-A]

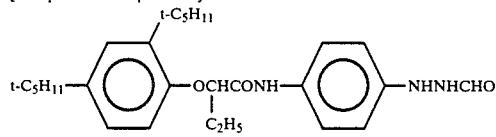

[Comparative compound-B]

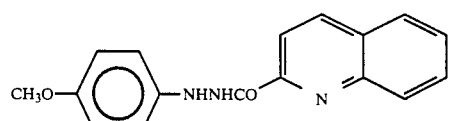

[Comparative compound-C]

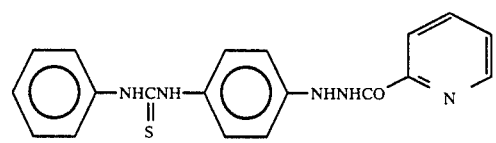

*Sensitivity (S): The sensitivity (log E) of blank is referred to as a standard. Sensitivity is represented by the difference therefrom. For example, the sensitivity of −1.0 means that the sensitivity is lower by 1.0 in terms of log E than that of blank, that is, it is ten times as low as the sensitivity of blank.
**Gradation (G): The gradient of a straight line formed by joining a point where density is 0.3 on characteristic curve to a point where density is 3.0. A larger value means a higher contrast.
***$\Delta S_{B-A}$: The difference between $S_B$ and $S_A$, said $S_B$ being sensitivity when development is carried out with an air-exhausted solution and said $S_A$ being sensitivity when development is carried out with a fresh solution.
****$\Delta S_{C-A}$: The difference between $S_C$ and $S_A$, said $S_C$ being sensitivity when development is carried out with an exhausted solution used for mass-processing and $S_A$ being sensitivity when development is carried out with a fresh solution.

EXAMPLE 2

An aqueous solution of silver nitrate and an aqueous solution of sodium chloride in the presence of $5.0 \times 10^{-6}$ mol (per mol of silver) of $(NH_4)_3RhCl_6$ were simultaneously mixed with an aqueous gelatin solution kept at 50° C. After the soluble salt was removed by a conventional method, gelatin was added thereto. Without carrying out chemical ripening, there was added 2-methyl-4-hydroxy-1,3,3a,7-tetraazaindene as a stabilizer. The resulting emuslion was a cubic monodispersed emulsion having a mean grain size of 0.15 μm.

Hydrazine compound identified in Table 2 was added to the emulsion. Further, 30 wt % (on a solid basis, based on the amount of gelatin) of polyethyl acrylate latex was added thereto, and 1,3-vinylsulfonyl-2-propanol as a hardening agent was also added thereto. A polyester support was coated with the resulting emulsion in such an amount as to give a coating weight of 3.8 g/m² in terms of Ag. The coating weight of gelatin was 1.8 g/m². Further, a layer containing gelatin (1.5 g/m²), polymethyl methacrylate particles (average particle diameter: 2.5 μm, 0.3 g/m²) as a matting agent, the following surfactants as coating aid, the following stabilizer and the following ultraviolet light absorbing dye as a protective layer, was coated thereon. The resulting material was dried.

| Surfactants: | |
|---|---|
| 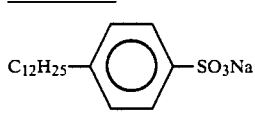 | 37 mg/m² |
| 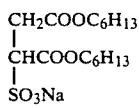 | 37 mg/m² |
| 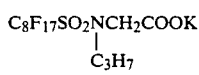 | 2.5 mg/m² |
| Stabilizer: | |
| Thioctic acid | 2.1 mg/m² |
| Ultraviolet Light Absorbing Dye: | |

-continued

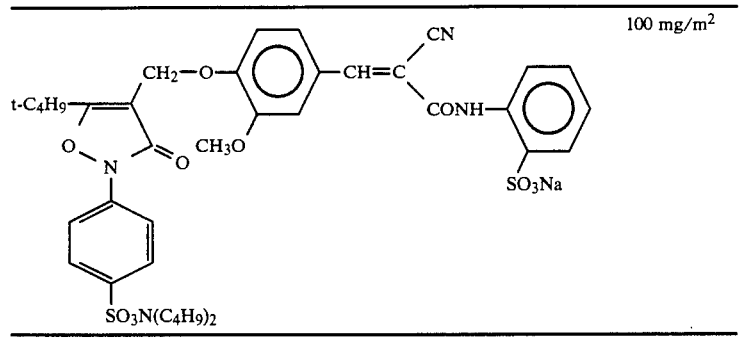 100 mg/m²

The samples were exposed through an optical wedge by using daylight printer p-607 (manufactured by Dainippon Screen KK), developed at 38° C. for 20 seconds, fixed with a fixer GR-F1 at 30° C. for 30 seconds, washed with water for 30 seconds and dried at 45° C. for 20 seconds.

The results of photographic characteristics are shown in Table 2.

It can be understood from the results of Table 2 that higher contrast can be obtained by the samples of the present invention as compared with the samples of Comparative Examples.

In the same manner as in Example 1, photographic performances are tested with exhausted solution. The samples of the present invention cause little fluctuation and give favorable results as shown in Table 2.

TABLE 2

| | | Nucleating agent | | Photographic characteristics with fresh solution | | Change of photographic characteristics with exhausted solution | |
|---|---|---|---|---|---|---|---|
| | | | | | | Air-exhausted | Exhausted solution used for mass- |
| | Sample No. | Kind | Amount (mol/mol of Ag) | Sensitivity (S)* | Gradation (G)** | solution $(\Delta s_{B-A})$*** | processing $(\Delta S_{C-A})$**** |
| 1 | Comp. Ex. 1 | blank | — | 0 | 4.8 | — | — |
| 2 | Comp. Ex. 2 | Comparative compound A | 1.5 × 10⁻³ | +0.16 | 9.2 | +0.12 | −0.09 |
| 3 | Comp. Ex. 3 | Comparative compound B | " | +0.14 | 7.8 | +0.10 | −0.10 |
| 4 | Comp. Ex. 4 | Comparative compound C | 3.0 × 10⁻⁴ | +0.06 | 7.3 | +0.19 | −0.13 |
| 5 | Invention 1 | Compound I-1 | " | +0.18 | 10.2 | +0.09 | −0.08 |
| 6 | Invention 2 | Compound I-2 | " | +0.18 | 11.5 | +0.08 | −0.08 |
| 7 | Invention 3 | Compound I-3 | " | +0.20 | 14.0 | +0.06 | −0.07 |
| 8 | Invention 4 | Compound I-4 | " | +0.21 | 15.3 | +0.06 | −0.06 |
| 9 | Invention 5 | Compound I-9 | " | +0.17 | 10.1 | +0.09 | −0.08 |
| 10 | Invention 6 | Compound I-19 | " | +0.18 | 13.7 | +0.07 | −0.07 |
| 11 | Invention 7 | Compound I-20 | " | +0.17 | 14.8 | +0.05 | −0.06 |
| 12 | Invention 8 | Compound I-21 | " | +0.18 | 12.3 | +0.07 | −0.08 |

While the invention has been described in detail and with reference to specific embodiments thereof, it will be apparent to one skilled in the art that various changes and modifications can be made therein without departing from the spirit and scope thereof.

What is claimed is:

1. A silver halide photographic material which comprises a support having thereon at least one hydrophilic colloid layer, wherein at least one hydrophilic colloid layer is a silver halide photographic emulsion layer, and at least one hydrophilic colloid layer contains a compound represented by the following general formula (I):

$$\begin{array}{c} A_1 \quad A_2 \\ | \quad | \\ R_1-N-N-G_1-X_1 \end{array} \quad (I)$$

wherein $A_1$ an $A_2$ both represent a hydrogen atom, or one of $A_1$ and $A_2$ is a hydrogen atom and the other is or an acyl group; $R_1$ represents an aliphatic group or an aromatic group; $G_1$ represents a carbonyl group, a sulphonyl group, a sulfinyl group, a sulfoxy group, a group of

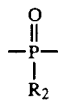

wherein $R_2$ is an alkoxy group or an alkoxy group or an aryloxy group, a group of

or an iminomethylene group; $X_1$ represents a nitrogen-containing heterocyclic ring; and at least one of $R_1$ and $X_1$ having an adsorption-accelerating group on silver halide which is represented by the formula: $Y_1$–$(L_2)_{\overline{l}}$ wherein $Y_1$ is an adsorption-accelerating group selected from the group consisting of a mercapto group, a group having a disulfide linkage, and a five-membered or six-membered nitrogen-containing heterocyclic group, $L_2$ is a divalent linking group, and l is 0 or 1.

2. The silver halide photographic material of claim 1, wherein $R_1$ is an aromatic group.

3. The silver halide photographic material of claim 2, wherein $R_1$ is an aryl group.

4. The silver halide photographic material of claim 1, wherein the compound is represented by the general formula (II):

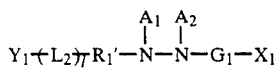
(II)

wherein $Y_1$ is an adsorption-accelerating group selected from the group consisting of mercapto groups, groups having a disulfide linkage, and five-membered and six-membered nitrogen-containing heterocyclic groups, $L_2$ is a divalent linking group, l is 0 or 1, and $R_1'$ is a group formed by removing one hydrogen atom from $R_1$ of general formula (I), provided that at least one of $R_1'$ and $L_2$ is a group which has a group capable of dissociated by an anion having a pKa of 6 or above and undergoes dissociation in the presence of an anion having a pKa of 6 or above..

5. The silver halide photographic material of claim 1, wherein the compound is represented by the general formula (III):

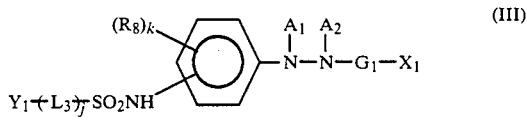
(III)

wherein $R_8$ has the same meaning as $R_1$ in the formula (I); k is 0, 1 or 2; $L_3$ is a divalent linking group; j is 0 or 1; and when k is 2, $R_8$ may be the same or different, and wherein $Y_1$ is an adsorption-accelerating group selected from the group consisting of mercapto groups, groups having a disulfide linkage, and five-membered and six-membered nitrogen-containing heterocyclic groups.

6. The silver halide photographic material of claim 1, wherein the amount of said compound represented by general formula (I) is $1 \times 10^{-5}$ to $1 \times 10^{-2}$ mol per mol of silver halide.

7. The silver halide photographic material of claim 1, wherein the support also has thereon a negative-type emulsion.

8. The silver halide photographic material of claim 1, wherein the silver halide has a mean grain size of not larger than 0.7 μm.

9. The silver halide photographic material of claim 1, wherein the silver halide has a mean grain size of not larger than 0.5 μm.

* * * * *